US00PP22519P2

(12) United States Plant Patent
Korlipara

(10) Patent No.: US PP22,519 P2
(45) Date of Patent: Feb. 21, 2012

(54) ***COREOPSIS* PLANT NAMED 'PUMPKIN PIE'**

(50) Latin Name: ***Coreopsis* spp.**
Varietal Denomination: Pumpkin Pie

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/927,226

(22) Filed: Nov. 9, 2010

(51) Int. Cl.
*A01H 5/00* (2006.01)

(52) U.S. Cl. ..... Plt./417

(58) Field of Classification Search ..... Plt./417
See application file for complete search history.

*Primary Examiner* — Annette Para
(74) *Attorney, Agent, or Firm* — Klarquist Sparkman, LLP

(57) ABSTRACT

A new and distinct *Coreopsis* plant named 'Pumpkin Pie' characterized by small daisy-type flowers that grow to 3.5 cm in diameter, flowers that are deep orange with red eyes, grass green foliage on short stems, flowering for the whole summer, and a dense, mounding habit.

1 Drawing Sheet

Botanical denomination: *Coreopsis* spp.

Variety designation: 'Pumpkin Pie'.

Parentage: (Coreopsis 'Little Penny' (U.S. Plant Pat. No.18,502)×*Coreopsis* 'Rum Punch' (U.S. Plant Pat. No. 18,889).

Cross reference to: Parents above and co-pending applications for *Coreopsis* 'Pineapple Pie' (Plant patent application Ser. No. 12/927,266) , 'Cherry Pie' (Plant patent application Ser. No. 12/927,270).

BACKGROUND OF THE INVENTION

The present invention relates to a new and distinct *Coreopsis* and given the cultivar name 'Pumpkin Pie'. *Coreopsis* is in the family Asteraceae. This new cultivar originated from a controlled cross of *Coreopsis* 'Rum Punch' (U.S. Plant Pat. No. 18,889) as the seed parent and *Coreopsis* 'Little Penny' (U.S. Plant Pat. No. 18,502) as the pollen parent. The breeding plan was to make a series like *Coreopsis* 'Little Penny'.

Compared to the seed parent, *Coreopsis* 'Little Penny', the new hybrid has flowers that are larger, and deep orange with red eyes rather than copper with small yellow eyes. Compared to the pollen parent, *Coreopsis* 'Rum Punch', the new cultivar has smaller flowers that are deep orange with red eyes rather than orangey-rose colored. The new cultivar has a smaller, tighter habit than *Coreopsis* 'Rum Punch'.

SUMMARY OF THE INVENTION

The following traits have been repeatedly observed and are determined to be the unique characteristics of the new variety. These characteristics in combination distinguish *Coreopsis* 'Pumpkin Pie' as a new and distinct cultivar:

1. small daisy-type flowers that grow to 3.5 cm in diameter,
2. flowers that are deep orange with red eyes,
3. grass green foliage on short stems,
4. flowering for the whole summer, and
5. a dense, mounding habit.

This new cultivar has been reproduced only by asexual propagation (cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE PHOTOGRAPH

The photograph shows a one-year-old *Coreopsis* 'Pumpkin Pie' growing in the ground in the trial field in August in Canby, Oreg.

DETAILED PLANT DESCRIPTION

The following is a detailed description of the new *Coreopsis* cultivar based on observations of four-month-old specimens growing in a one gallon container in a cool greenhouse in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart, $5^{th}$ edition.

Plant:

*Type.*—Herbaceous perennial.
*Hardiness.*—USDA Zones 7 to 9.
*Size.*—20 cm wide and 21 cm tall to top of inflorescences.
*Form.*—Mound.
*Vigor.*—Excellent.
*Roots.*—Fibrous, stems root easily from stem cuttings.

Stem:

*Type.*—Ascending.
*Size.*—12 cm tall to where branches for flowering and 5 mm wide.
*Number of stems from the crown.*—1.
*Internode length.*—1 to 2.8 cm.
*Surface.*—Glabrous.
*Color.*—Yellow Green 137A.

Leaf:

*Type.*—Simple.

*Shape.*—Linear except near base where sometimes pinnatifid with 2 linear side lobes.

*Arrangement.*—Opposite.

*Size.*—Grows to 5 cm long and 6 mm wide (3.5 cm wide if pinnatifid).

*Margins.*—Entire.

*Petiole.*—Sessile.

*Apex.*—Acute.

*Base.*—Cuneate clasping.

*Surface texture.*—Glabrous on top and bottom sides.

*Venation.*—Pinnate.

*Color.*—Topside Yellow Green 137A, bottom side Yellow Green 146A.

Inflorescence:

*Type.*—Long stalked terminal heads of daisy type inflorescences.

*Peduncle.*—Grows to 6 cm long, 1 mm wide, glabrous, Green 137A.

*Size.*—Grows to 3.5 cm wide and 9 mm deep.

*Immature.*—Globular, 5 mm wide and 4 mm deep, Yellow Green 146B on the sides and Greyed Purple N186C on top, glabrous.

*Receptacle.*—Disc shaped, 3 mm wide and 1.5 mm deep, Yellow Green 146A.

*Phyllary.*—In 2 series; first series closet to ray florets 4 mm deep and 10 mm wide, 8 in number, each 5.5 mm long and 2 mm wide, ovate, margin entire, tip acute, glabrous on both sides, both sides Grey Purple 187A on the tip and Greyed Orange 163A on top half and Yellow Green 146A on bottom half; lower series in an area 3 mm deep and 6 mm wide, 8 in number, 2 mm long and 1 mm wide, each ovate, margin entire, tip acute, both sides glabrous and Yellow Green 146A.

*Lastingness.*—Each inflorescence lasts about a week on the plant.

Florets:

*Type.*—Composite.

*Ray florets.*—8 in number with no pistil or stamen, grows to 17 mm long, 10 mm wide, obovate with the tip three-lobed with lobe tips obtuse and the central lobe the longest and cupped down, sometimes notched, margins entire, glabrous on both sides, sometimes with linear projection from above the claw, 7 mm long and 1 mm wide; topside mostly Greyed Orange 167B with tip tinted Greyed Orange 177B and basal spot Greyed Purple 187B, bottom side Greyed Orange 165C.

*Disc.*—Conic, deeper with maturity, 6 mm wide and becoming 4 mm deep with maturity, Greyed Purple 187A before opening, after opening Yellow Orange 21B with a background of Greyed Purple 187A.

*Disc florets.*—Tubular, with stamen and pistil, about 75 in number, 5.5 mm long and 1 mm wide, tubular; corolla 4 mm long, Greyed Orange 175A on the 4 lobes to Yellow Orange 23A on the upper tube to Green Yellow 1C on the lower tube; pistil 1, 6 mm long, ovary 1.4 mm long, Green Yellow 1C, style 4 mm long, with extruding, 2-branched stigma, stigma and style Yellow Orange 21B; stamen 5, anthers 1.3 mm long, Greyed Purple 187A, pollen Yellow 10A.

*Bloom period.*—June through September in Canby, Oreg.

*Fragrance.*—Light, Chrysanthemum-like.

*Seed.*—None seen.

*Fertility.*—Unknown.

Disease and pests: *Coreopsis* are susceptible to mildew and fungal spots. No resistance is known for this variety.

I claim:

1. A new and distinct *Coreopsis* plant as herein illustrated and described.

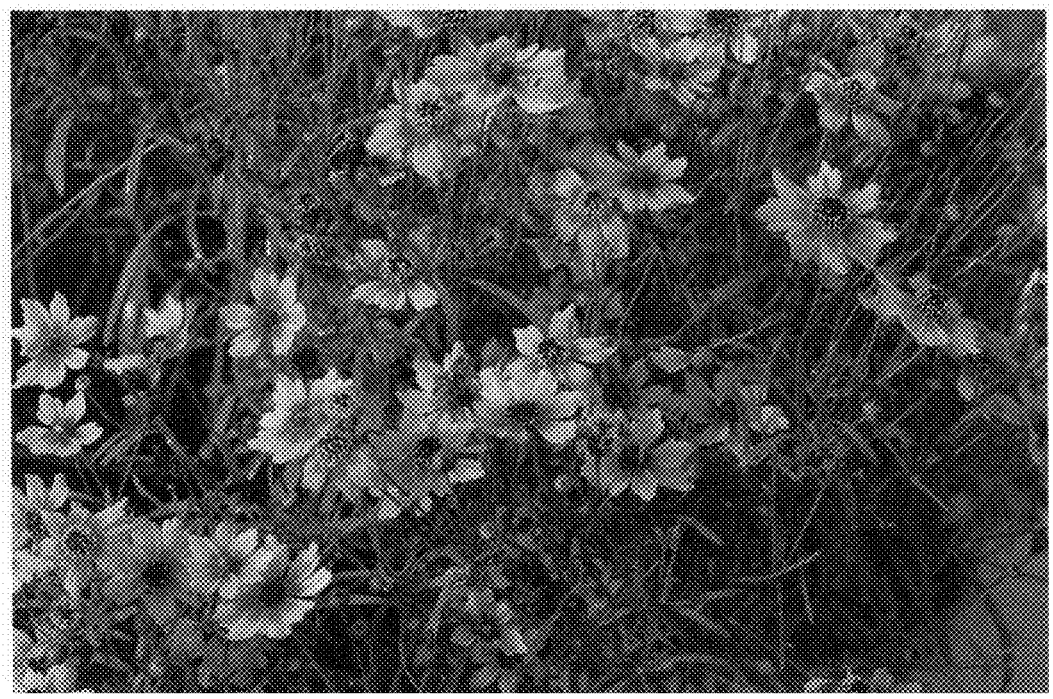

* * * * *